United States Patent [19]

Skaling

[11] 4,068,525
[45] Jan. 17, 1978

[54] PORTABLE TENSIOMETER FOR SOIL MOISTURE MEASUREMENT

[75] Inventor: Percy E. Skaling, Santa Barbara, Calif.

[73] Assignee: Soilmoisture Equipment Corporation, Santa Barbara, Calif.

[21] Appl. No.: 724,628

[22] Filed: Sept. 20, 1976

[51] Int. Cl.² .............................................. G01N 25/56
[52] U.S. Cl. ............................................................. 73/73
[58] Field of Search .......................... 73/73; 239/63, 64

[56] References Cited

U.S. PATENT DOCUMENTS

| 2,023,490 | 12/1935 | Richards | 73/73 |
| 3,939,699 | 2/1976 | McCormick | 73/73 |
| 3,961,753 | 6/1976 | Sears | 73/73 X |

Primary Examiner—Jerry W. Myracle
Attorney, Agent, or Firm—Fulwider, Patton, Rieber, Lee & Utecht

[57] ABSTRACT

A portable tensiometer for measuring the moisture content of soil, including an elongated housing tube having a hollow porous tip mounted thereon for insertion in the soil, and a hollow handle element having a vacuum gauge secured to one end and a cylinder defining a chamber of adjustable volume at the other end. Capillary tubing, which connects the interior of the porous tip to the adjustable-volume chamber and to the vacuum gauge to form a sealed, normally water-filled system, and the use of a minimal volume of water in the instrument minimizes errors due to changes in temperature to which the instrument is subjected.

8 Claims, 2 Drawing Figures

U.S. Patent     Jan. 17, 1978     4,068,525
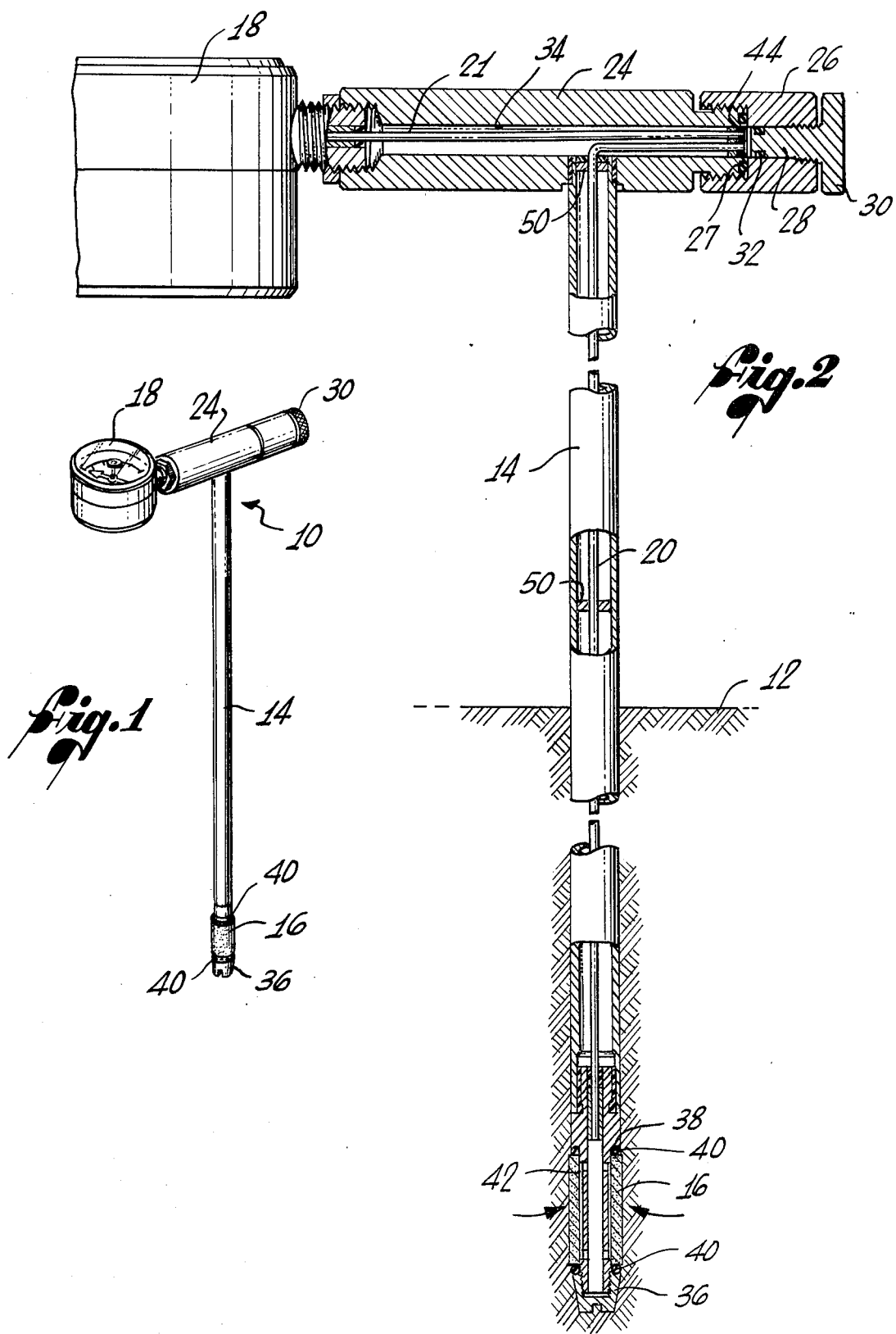

PORTABLE TENSIOMETER FOR SOIL MOISTURE MEASUREMENT

BACKGROUND OF THE INVENTION

This invention relates generally to soil moisture measuring instruments commonly known as tensiometers, and, more particularly, to tensiometers which are intended to be used as portable instruments rather than installed permanently in an operative position inserted in the soil.

As is well known, if the moisture content of soil can be accurately monitored, irrigation can be controlled to produce a desired rate of plant growth. Instruments of the tensiometer type have been used for a number of years for this purpose. Basically, a conventional tensiometer comprises a sealed tube defining a chamber which is normally completely filled with water, a hollow porous tip on one end of the tube, and a vacuum gauge connected to the water chamber. The porous tip is inserted in the soil and establishes liquid contact between the water in the tube and films of moisture in the soil surrounding the tip.

Relatively dry soil tends to pull water from the tube through the porous tip, but, since the tube is sealed, only a minute amount of water is actually withdrawn, and the water in the tube is "stretched" by the pulling effect of the dry soil, thus creating a measurable subatmospheric pressure in the tube. Higher moisture contents in the soil produce correspondingly less vacuum in the tube, and completely saturated soil registers substantially zero vacuum.

Since it may take a substantial time for the water in the tensiometer tube to reach a stable equilibrium condition with respect to the moisture in the soil, many tensiometers are utilized as permanently installed instruments, so that immediate readings of the soil moisture content can be obtained. Clearly, however, there are significant economic disadvantages in having to purchase and maintain a relatively large number of tensiometer instruments. There is therefore also a need for portable tensiometers, which an be transported between selected measuring sites, and inserted in the soil to obtain the desired soil moisture measurements. Portable tensiometers can include a null-adjustment device which allows the equilibrium condition to be reached more rapidly than would otherwise be possible. Essentially, the null-adjustment device includes a chamber within the enclosed tensiometer water system, the volume of which is adjustable by a movable piston.

Even with the inclusion of such a null-adjustment device, however, portable tensiometers available prior to this invention have suffered one serious shortcoming. A portable tensiometer is usually carried between measuring sites in the cab of a truck or other vehicle, and may at these times be subjected to relatively high temperatures. The soil, on the other hand, will be relatively cool, and the instrument will therefore be subjected to a sudden lowering in temperature on insertion in the soil. Since water has a thermal coefficient of expansion which is typically many times greater than that of the metal tube usually used to enclose the water, this sudden lowering of temperature will result in a substantial contraction of the water within the tube. This, in turn, results in a substantial error in the vacuum measurement. Similar errors can result from largely unpredictable temperature variations, caused by moving clouds, for example, while a measurement is being taken. Since vacuum gauges used in portable tensiometers typically require a flow of only approximately 0.1 milliliter of water to register a full-scale change in pressure from atmospheric pressure (0 centibars) to a vacuum of 100 centibars, it will be appreciated that these temperature variations can result in substantial errors in the readings obtained.

Accordingly, there is a real need in the field of soil moisture measurement for a portable instrument which eliminates or minimizes errors resulting from changes in temperature to which the instrument is subjected. The present invention fulfills this need.

SUMMARY OF THE INVENTION

The present invention resides in a soil moisture-indicating tensiometer having the usual porous-tipped tube and vacuum gauge, but in which the total volume of water is reduced to a minimum. Since the total volume of water is minimized, changes in volume due to differential thermal expansion and contraction of the water are also minimized, as are the resultant effects on the vacuum gauge readings.

Basically, and in general terms, the portable tensiometer of the present invention includes an elongated housing tube having a hollow porous tip secured to one end to be inserted in the soil, the porous tip in part defining the walls of a first chamber; means attached to the housing tube and defining a second chamber of adjustable volume to be used for null adjustment; a vacuum gauge; and capillary tube means connecting the first chamber, the second chamber and the vacuum gauge as a sealed system normally filled with water. The capillary tube means minimizes the volume of water in the tensiometer, and thereby minimizes errors due to differential expansion and contraction of the water with respect to its containing tube.

More specifically, the housing tube is attached by its upper end, remote from the porous tip, to a hollow handle element, forming a T-shaped structure with the housing tube. The means defining the second chamber of adjustable volume includes a cylinder attached to one end of the handle element, and a plunger movable in the cylinder by means of a rotatable adjusting knob. The capillary tube means is disposed partly inside the housing tube and partly inside the handle element. One section of the capillary tube means connects the first chamber, i.e., the interior of the porous tip, to the cylinder in the handle element, and a second section connects the cylinder to the vacuum gauge, which is secured to the other end of the handle element.

In accordance with another aspect of the invention, the first section of the capillary tube means is retained at the approximate axial center of the housing tube by a plurality of annular spacers. Thus, there is a substantial air space separating the housing tube from the capillary tube, thereby thermally insulating the capillary tube from transient temperature changes to which the instrument is subjected, as by the movement of clouds across the sun.

Other aspects and advantages of the invention will become apparent from the following more detailed description, taken in conjunction with the accompanying drawings.

BRIEF DESCRIPTION OF THE DRAWINGS

FIG. 1 is perspective view of a portable tensiometer embodying the present invention; and FIG. 2 is an enlarged, fragmentary, elevational view, shown partly in section, of the tensiometer of FIG. 1 inserted in the soil in an operative position.

DETAILED DESCRIPTION

As shown in the drawings for purposes of illustration, the present invention resides in a portable tensiometer, indicated generally by reference numeral 10, which can be inserted in the soil, indicated at 12, in order to obtain a reading of the moisture content of the soil. Basically, and like other tensiometers of the same general type, the instrument of this invention includes a tube 14 having a hollow porous tip 16 which is inserted in the soil 12, and a vacuum gauge 18 connected to the interior of the porous bulb by, as will be described, a sealed, water-filled system. The porous tip 16 establishes liquid contact with moisture in the soil 12 and the soil exerts a pull on the water in the instrument, to a degree dependent on the relative dryness of the soil, the pull being measurable by the vacuum gauge 18.

In accordance with the present invention, the water at the porous tip 16 is connected with the vacuum gauge 18 by means of two sections of capillary tubing 20 and 21 which minimize the total water volume of the instrument, and which also minimize possible errors in moisture readings due to changes in temperatures to which the instrument is subjected. The tube 14 serves only as a housing, and not as a water-containing tube as in other instruments of this type.

The tube 14 is secured to a hollow handle element 24 at the end of the tube remote from the porous tube 16, forming a T-shaped structure with a handle element. One end of the handle element 24 has a reduced-diameter portion which is threaded to engage a relatively short cylinder 26, and an O-ring seal 27 is provided to seal the interior of the cylinder 26 from the atmosphere. The cylinder 26 is internally threaded to receive a plunger 28 having an external adjusting knob 30 integral therewith. Another O-ring seal 32 ensures sealing contact between the plunger 28 and the cylinder 26, and rotation of the adjusting knob 30 allows adjustment of the volume of the chamber enclosed by the cylinder and plunger. A bore 34 through the handle element 24 extends from the end attached to the cylinder 26 to the opposite end, which is internally threaded to receive the dial gauge 18.

The porous tip 16 is essentially a hollow cylinder which may be formed from any of a wide variety of materials, including ceramics, the only requirement being that the "bubbling pressure", the pressure below which air will not pass through the wettened pores of the material, must be greater than normal atmospheric pressure, to prevent bubbles of air from entering the instrument 10. The tip 16 is secured to the tube 14 by means of a threaded cap 36 which holds the porous tip 16 against an annular shoulder 38 formed on the tube. Two O-ring seals 40, one at each end of the porous tip 16, function to prevent leakage around the ends of the tip.

The capillary tubing used in the instrument 10 includes the first section 20, which is connected to communicate with a chamber 42 formed interiorly of the porous tip 16, and extends through the center of the tube 14 into the bore 34 of the handle element 24, and thence through a seal 44 to the interior of the cylinder 26. The second section of capillary tubing 21 extends through the bore 34 from the interior of the cylinder 26 to the dial gauge 18.

Since portable tensiometers of this general type are typically transported from measuring site to measuring site within the cab of a truck or some other vehicle which may be exposed to relatively high temperatures, the instrument may be subjected to a substantial drop in temperature when inserted in the soil. Changing weather conditions while measurements are being taken can also cause substantial variations in the temperature of the instrument. Typically, the tubes used to enclose water in a conventional tensiometer have a thermal coefficient of expansion much less than that of the water itself. Consequently, changes in temperature result in corresponding changes in the volume of water, these showing up as erroneous vacuum readings on the gauge 18. Preferably, the dial gauge 18 is of the Bourdon type, which requires a flow of only approximately 0.1 ml of water to register a full-scale change in pressure from atmospheric pressure (0 centibars) to a vacuum of 100 centibars. The use of the capillary tubes 20 and 21, however, reduces the change in volume of the system due to temperature changes to an absolute minimum.

The effects of temperature changes occuring while measurements are in progress are further reduced due to the fact that the capillary tube 20 is retained at approximately the axial center of the housing tube 14 by means of annular spacers 50 disposed along the tube. Thus, there is a substantial air space between the capillary tube section 20 and the housing tube 14, to insulate the water in the instrument from sudden temperature changes.

In use, the instrument 10 is placed in a hole in the soil 12, after forming the hole with a coring tool (not shown), and initially left for a few minutes to help stabilize its temperature and its equilibrium relationship with the soil moisture. If the soil is completely saturated, the reading on the dial gauge 18 will remain at zero. However, if the soil is dry to some degree, the vacuum reading on the gauge 18 will begin to rise as the soil exerts a pull on the water in the instrument. A stable reading can be obtained more rapidly by adjusting the null-adjustment knob 30 initially to increase the volume of the cylinder 26, thereby placing an additional pull on the gauge 18. If, after the initial adjustment, the reading on the gauge continues to rise, a further increase in volume is effected using the knob 30. If, however, the upward trend of the gauge 18 reverses and the reading begins to fall, the knob 30 can be used to reduce the volume of the cylinder 26 and thereby "bracket" the true reading and converge on it more rapidly.

It will be appreciated from the foregoing that the present invention represents a significant advance in the field of portable tensiometers. In particular, by minimizing the volume of water within the instrument, the present invention minimizes the effects of temperature variation on the readings obtained, and results in a highly practical portable instrument. It will also be appreciated that, although the invention has been described in detail with reference to a particular embodiment illustrated by way of example, various changes and modifications may be made without departing from the spirit and scope of the invention. Accordingly, the invention is not to be limited except as by the appended claims.

I claim:

1. A portable tensiometer for measuring soil moisture content, comprising:
    an elongated housing tube having a hollow porous tip secured to one end to be inserted in the soil, said porous tip in part defining the walls of a first chamber;

means attached to said housing tube and defining a second chamber of adjustable volume; p1 a vacuum gauge; and capillary tube means disposed in said housing tube and connecting said first chamber, said second chamber and said vacuum gauge as a sealed system normally filled with water;

whereby said capillary tube means minimizes the volume of water in said tensiometer and therefore minimizes errors due to temperature changes to which said tensiometer is subjected, the effects of any temperature changes being further minimized by the location of said capillary tube means within said housing tube, and whereby said means defining a second chamber of adjustable volume is operable to obtain more rapidly a stable reading on said vacuum gauge.

2. A portable tensiometer for measuring soil moisture content, comprising:

an elongated housing tube having a hollow porous tip secured to one end to be inserted in the soil, the interior of said porous tip in part defining the walls of a first chamber inside said tube;

a handle element secured to the end of said housing tube remote from said porous tip, said handle element having a bore therein communicating with the interior of said housing tube;

a vacuum gauge secured to one end of said handle element;

a cylinder secured to the other end of said handle element;

a plunger adjustable engaged in said cylinder to form a second chamber of adjustable volume;

a first section of capillary tubing connecting said first chamber to said second chamber and disposed within said housing tube and said bore of said handle element; and a second section of capillary tubing connecting said second chamber to said vacuum gauge and disposed in said bore of said handle element;

whereby said sections of capillary tubing minimize the volume of water in said tensiometer and minimize errors due to differential expansion and contraction of the water caused by temperature changes, and whereby said plunger is adjustable within said cylinder in order to converge upon a stable vacuum gauge reading more rapidly.

3. A portable tensiometer as set forth in claim 2, and further including a plurality of annular spacers disposed along said housing tube to support said first section of capillary tubing substantially in the axial center of said housing tube, thereby providing an insulating air space to minimize further the effects of temperature changes on the readings of the instrument.

4. A portable tensiometer for measuring soil moisture content, having a hollow porous bulb to be inserted in the soil, a vacuum gauge, and sealed means normally filled with water connecting said porous bulb to said vacuum gauge, wherein the improvement comprises:

an elongated housing tube on which said porous bulb is mounted; and capillary tube means disposed in said housing tube, forming substantially all of said sealed means, and connecting said bulb to said vacuum gauge using a minimum volume of water, whereby errors in vacuum gauge readings due to temperature changes are minimized by the low volume of water and by the location of said capillary tube means within said housing tube.

5. A portable tensiometer as set forth in claim 4, wherein said sealed means further includes null adjustment means comprising an adjustable-volume chamber communicating with said capillary tube means.

6. A portable tensiometer for measuring soil moisture content, comprising:

an elongated housing tube having a hollow porous tip secured to one end to be inserted in the soil, said porous tip in part defining the walls of a first chamber;

means attached to said housing tube and defining a second chamber of adjustable volume;

a vacuum gauge; and capillary tube means connecting said first chamber, said second chamber and said vacuum gauge as a sealed system normally filled with water, wherein said capillary tube means comprises a first section connecting said first chamber to said second chamber and second section connecting said second chamber to said vacuum gauge;

whereby said capillary tube means minimizes the volume of water in said tensiometer and minimizes errors due to temperature changes to which said tensiometer is subjected, and whereby said means defining a second chamber of adjustable volume is operable to obtain more rapidly a stable reading on said vacuum gauge.

7. A portable tensiometer for measuring soil moisture content, comprising:

an elongated housing tube housing a hollow porous tip secured to one end to be inserted in the soil, said porous tip in part defining the walls of a first chamber;

means attached to said housing tube and defining a second chamber of adjustable volume;

a vacuum gauge;

capillary tube means connecting said first chamber, said second chamber and said vacuum gauge as a sealed system normally filled with water; and at least one spacer supporting said capillary tube means within said housing tube and maintaining a substantial air space therebetween, whereby said capillary tube means is insulated by air space from effects of external temperature changes;

whereby said capillary tube means minimizes the volume of water in said tensiometer and minimizes errors due to temperature changes to which said tensiometer is subjected, and whereby said means defining second chamber of adjustable volume is operable to obtain more rapidly a stable reading on said vacuum gauge.

8. A portable tensiometer for measuring soil moisture content, having a hollow porous bulb to be inserted in the soil, a vacuum gauge, and sealed means normally filled with water connecting said porous bulb to said vacuum gauge, wherein the improvement comprises:

an elongated housing tube on which said porous bulb is mounted;

capillary tube means disposed in said housing tube, forming part of said sealed means, and connecting said bulb to said vacuum gauge using a minimum volume of water, whereby errors in vacuum gauge readings due to temperature changes are minimized; and at least one spacer located in said housing tube to retain said capillary tube means in a substantially axial position with respect thereto, whereby said capillary tube means is insulated from temperature changes, and any errors resulting from such changes are further reduced.

* * * * *

UNITED STATES PATENT AND TRADEMARK OFFICE
CERTIFICATE OF CORRECTION

PATENT NO. : 4,068,525
DATED : January 17, 1978
INVENTOR(S) : PERCY E. SKALING

It is certified that error appears in the above-identified patent and that said Letters Patent are hereby corrected as shown below:

Column 3, line 26, "temperatures" should be --temperature--.

line 32, "a" (second occurrence) should be --the--.

Claim 1, line 8, delete "pl" and begin a new paragraph with "a vacuum gauge;".

Claim 2, line 15, "adjustable" should be --adjustably--.

Claim 6, line 15, after "and", insert --a--.

Claim 7, line 3, "housing" (second occurrence) should be --having--;

line 22, after "defining" insert --a--.

Signed and Sealed this

Thirteenth Day of June 1978

[SEAL]

Attest:

RUTH C. MASON
*Attesting Officer*

DONALD W. BANNER
*Commissioner of Patents and Trademarks*